(12) United States Patent
Allen

(10) Patent No.: US 11,791,024 B2
(45) Date of Patent: Oct. 17, 2023

(54) IMPLEMENTING LOCALIZED DEVICE SPECIFIC LIMITATIONS ON ACCESS TO PATIENT MEDICAL INFORMATION

(71) Applicant: Merative US L.P., Ann Arbor, MI (US)

(72) Inventor: Corville O. Allen, Morrisville, NC (US)

(*) Notice: Subject to any disclaimer, the term of this patent is extended or adjusted under 35 U.S.C. 154(b) by 1007 days.

(21) Appl. No.: 15/412,895

(22) Filed: Jan. 23, 2017

(65) Prior Publication Data

US 2018/0211005 A1   Jul. 26, 2018

(51) Int. Cl.
*G16H 10/60* (2018.01)
*G06F 21/62* (2013.01)

(52) U.S. Cl.
CPC ......... *G16H 10/60* (2018.01); *G06F 21/6245* (2013.01)

(58) Field of Classification Search
CPC ............................ G16H 10/60; G06F 21/6245
See application file for complete search history.

(56) References Cited

U.S. PATENT DOCUMENTS

| | | | |
|---|---|---|---|
| 7,725,332 | B1 | 5/2010 | Soong |
| 7,805,377 | B2 | 9/2010 | Felsher |
| 8,275,803 | B2 | 9/2012 | Brown et al. |
| 8,498,884 | B2 | 7/2013 | Maitland et al. |
| 9,794,606 | B2 * | 10/2017 | Park ................... H04N 21/6334 |
| 2008/0306872 | A1 | 12/2008 | Felsher |
| 2009/0037224 | A1 * | 2/2009 | Raduchel ............... G06Q 50/24 |
| | | | 705/3 |
| 2009/0287678 | A1 | 11/2009 | Brown et al. |
| 2009/0292561 | A1 | 11/2009 | Itoh |
| 2011/0022414 | A1 | 1/2011 | Ge et al. |
| 2011/0066587 | A1 | 3/2011 | Ferrucci et al. |
| 2011/0125734 | A1 | 5/2011 | Duboue et al. |

(Continued)

OTHER PUBLICATIONS

Alhaqbani, B., Colin F., Access Control Requirements for Processing Electronic Health Records, Sep. 2007, BPM 2007 Workshops, pp. 371-382 (Year: 2007).*

(Continued)

*Primary Examiner* — Robert A Sorey
*Assistant Examiner* — Kimberly A. Sass
(74) *Attorney, Agent, or Firm* — Stephen J Walder, Jr.

(57) ABSTRACT

A mechanism is provided in a data processing system to implement localized device specific limitations on access to patient medical information. An authorizing device receives a request from a requestor device via a dose proximity communication protocol requesting to access an electronic medical record (EMR) associated with a patient. The authorizing device receives user input via a user interface specifying conditions for permitting access to the EMR. The authorizing device transmits an access authorization request to a patient registry system requesting the patient registry system to provide access to the EMR associated with the patient in accordance with the conditions for permitting access specified by the user input. The patient registry system generates a temporary access data structure based on the specified conditions. The patient registry system processes a subsequent request from the requestor device to access the EMR in accordance with the temporary access data structure.

19 Claims, 4 Drawing Sheets

(56) References Cited

U.S. PATENT DOCUMENTS

| | | | | |
|---|---|---|---|---|
| 2011/0302632 | A1* | 12/2011 | Garrett | H04L 63/205 726/4 |
| 2012/0203798 | A1 | 8/2012 | Gifford et al. | |
| 2013/0007055 | A1 | 1/2013 | Brown et al. | |
| 2013/0018652 | A1 | 1/2013 | Ferrucci et al. | |
| 2013/0066886 | A1 | 3/2013 | Bagchi et al. | |
| 2013/0227285 | A1* | 8/2013 | Bracher | G06F 21/6218 713/168 |
| 2014/0180719 | A1 | 6/2014 | Bell et al. | |
| 2014/0278524 | A1* | 9/2014 | Vaglio | G06Q 50/24 705/3 |
| 2014/0343962 | A1 | 11/2014 | Xu et al. | |
| 2015/0046192 | A1* | 2/2015 | Raduchel | G16H 10/60 705/3 |
| 2015/0250396 | A1* | 9/2015 | Ahmed | A61B 5/02416 600/508 |
| 2015/0302221 | A1* | 10/2015 | Kurian | G06F 21/10 726/30 |
| 2015/0347689 | A1* | 12/2015 | Neagle | A61B 5/0002 705/3 |
| 2017/0161439 | A1* | 6/2017 | Raduchel | G06Q 10/063 |
| 2017/0206332 | A1* | 7/2017 | Piccin | G16H 15/00 |
| 2017/0230369 | A1* | 8/2017 | Chanda | G06F 21/10 |

OTHER PUBLICATIONS

"Patient Access Controls", Australian Digital Health Agency, National E-Health Transition Authority (nehta), http://www.nehta.gov.au/using-the-my-health-record-system/maintaining-digital-health-in-your-practice, retrieved from the Internet May 25, 2016, 2 pages.

Alhaqbani, Bandar et al., "Access Control Requirements for Processing Electronic Health Records", Springer-Verlag Berlin Heidelberg, BPM 2007 Workshops, LNCS 4928, (month unknown) 2008, pp. 371-382.

Caine, Kelly et al., "Patients want granular privacy control over health information in electronic medical records", J Am Med Inform Assoc, http://www.medscape.com/viewarticle/776925, vol. 20, No. 1, (month unknown) 2013, pp. 7-15.

Ferreira, Ana et al., "Access Control: how can it improve patients' healthcare?", IOS Press, Jun. 2007, 12 pages.

Gajanayake, Randike et al., "Privacy Oriented Access Control for Electronic Health Records", ACM, DUMW2012, Lyon, France, Apr. 16, 2012, 8 pages.

High, Rob, "The Era of Cognitive Systems: An inside Look at IBM Watson and How it Works", IBM Corporation, Redbooks, Dec. 12, 2012, 16 pages.

Mccord, M.C, et al., "Deep parsing In Watson", IBM J. Res. & Dev. vol. 56 No. 3/4 Paper 3, May/Jul. 2012, pp. 3:1-3:15.

Wiech, Dean, "Role-based access control in healthcare", Healthcare IT News, http://www.healthcareitnews.com/blog/role-based-access-control-healthcare, Aug. 26, 2013, 20 pages.

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, pp. 1-14.

* cited by examiner

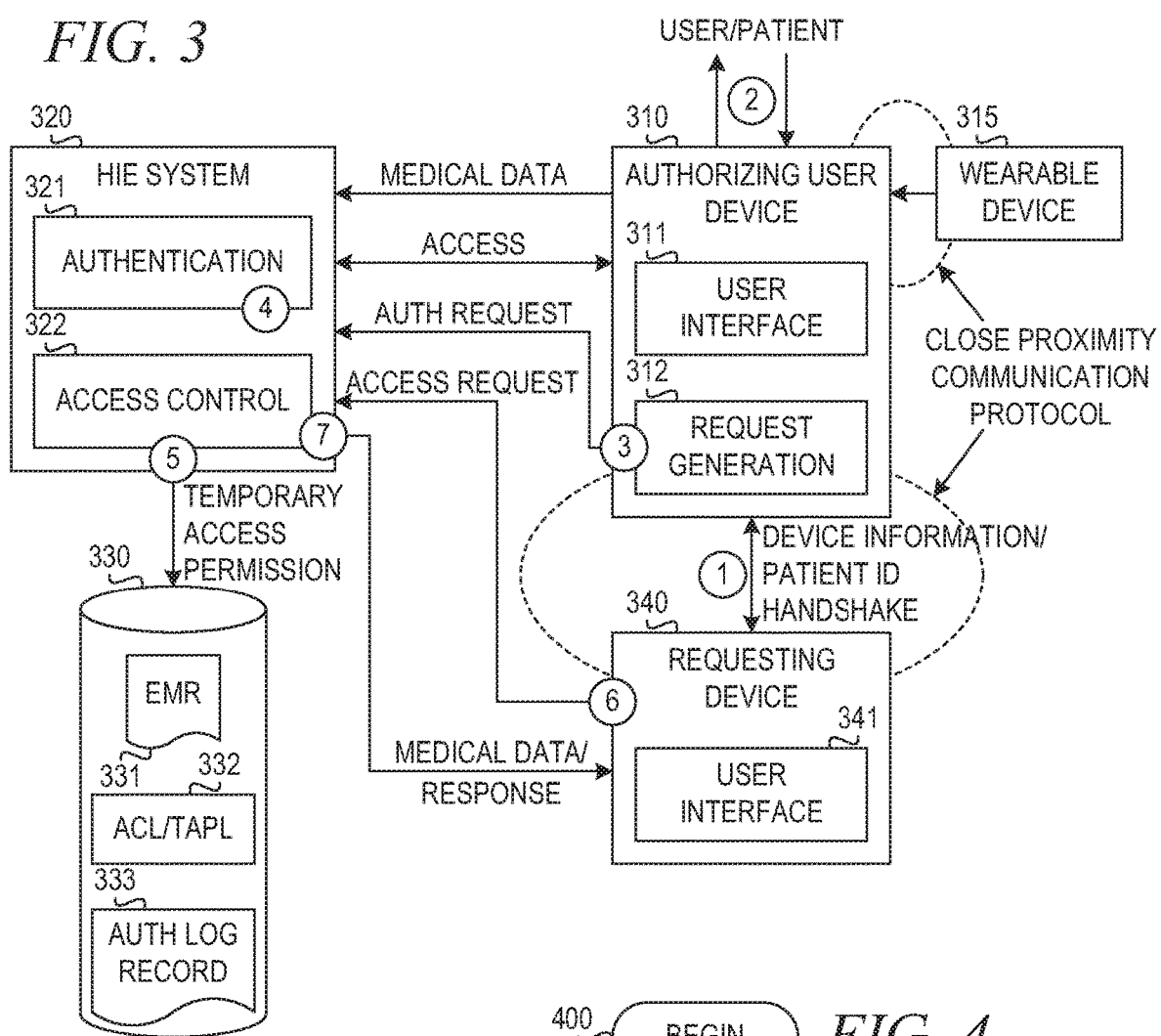
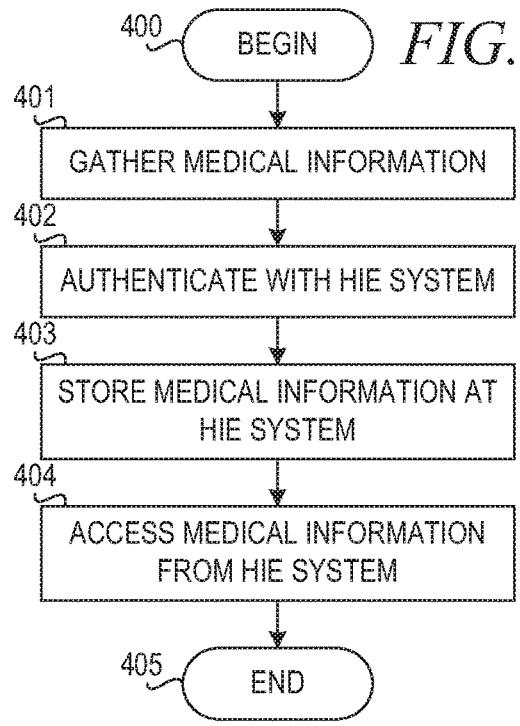

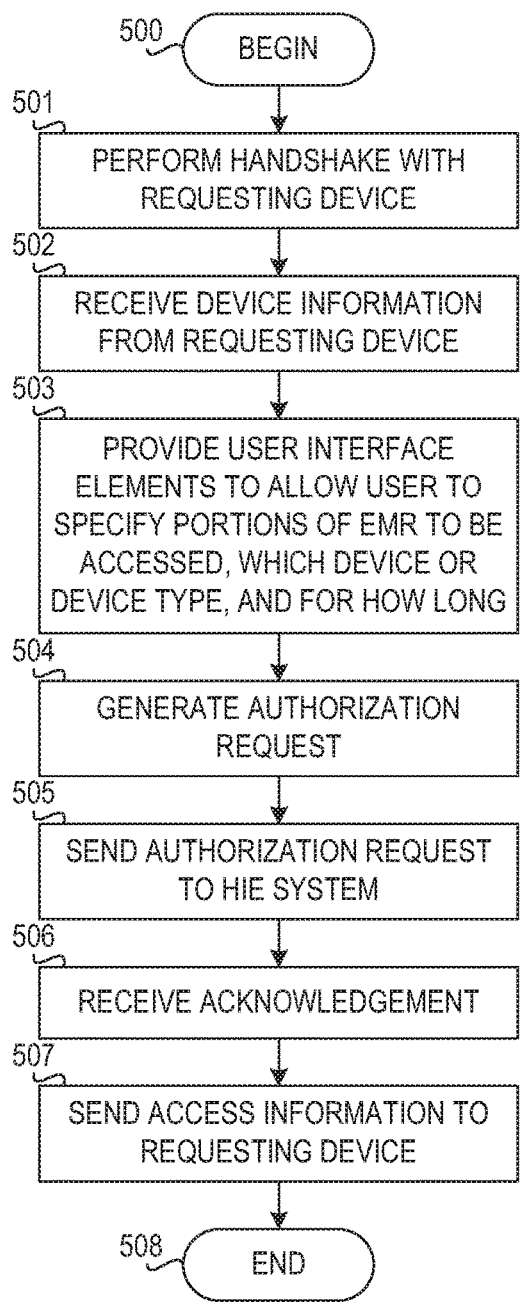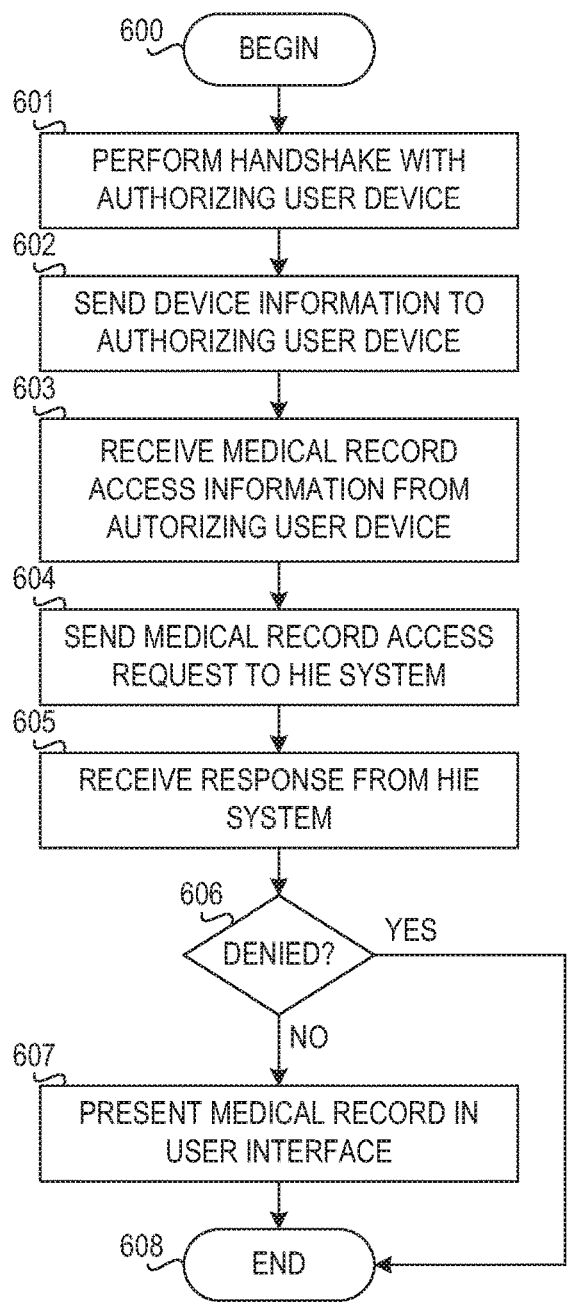

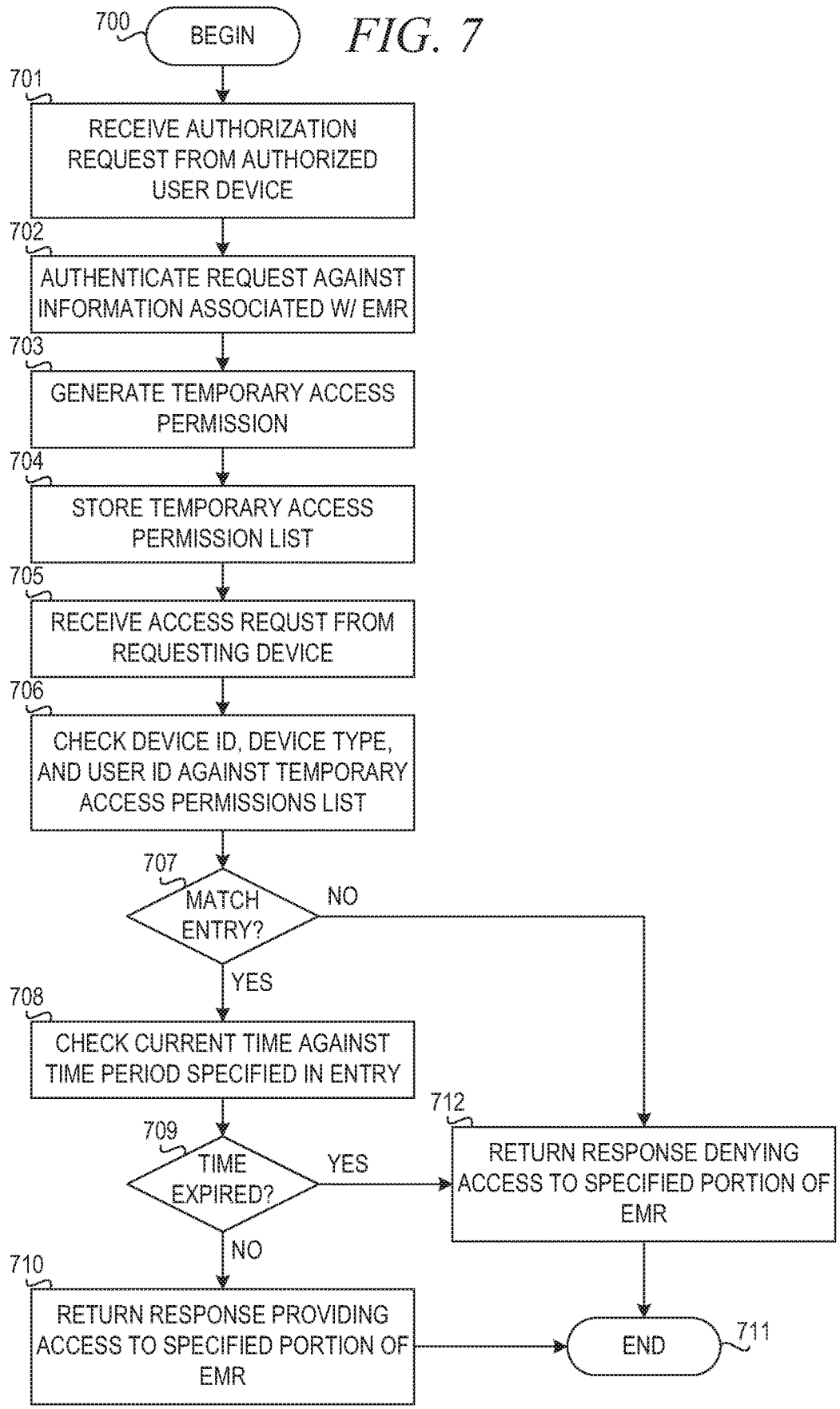

IMPLEMENTING LOCALIZED DEVICE SPECIFIC LIMITATIONS ON ACCESS TO PATIENT MEDICAL INFORMATION

BACKGROUND

The present application relates generally to an improved data processing apparatus and method and more specifically to mechanisms for implementing localized device specific limitations on access to patient medical information.

An electronic health record (EHR), or electronic medical record (EMR), refers to the systematized collection of patient and population electronically-stored health information in a digital format. These records can be shared across different health care settings. Records are shared through network-connected, enterprise-wide information systems or other information networks and exchanges. EMRs may include a range of data, including demographics, medical history, medication and allergies, immunization status, laboratory test results, radiology images, vital signs, personal statistics like age and weight, and billing information.

EMR systems are designed to store data accurately and to capture the state of a patient across time. An EMR system eliminates the need to track down a patient's previous paper medical records and assists in ensuring data is accurate and legible. It can reduce risk of data replication as there is only one modifiable file, which means the file is more likely up to date, and decreases risk of lost paperwork. Due to the digital information being searchable and in a single file, EMRs are more effective when extracting medical data for the examination of possible trends and long term changes in a patient. Population-based studies of medical records may also be facilitated by the widespread adoption of EMRs.

Health information exchange (HIE) is the mobilization of health care information electronically across organizations within a region, community or hospital system. In practice the term HIE may also refer to the organization that facilitates the exchange. HIE provides the capability to electronically move clinical information among different health care information systems. The goal of HIE is to facilitate access to and retrieval of clinical data to provide safer and more timely, efficient, effective, and equitable patient-centered care. HIE is also useful to public health authorities to assist in analyses of the health of the population.

HIE systems facilitate the efforts of physicians and clinicians to meet high standards of patient care through electronic participation in a patient's continuity of care with multiple providers. Secondary health care provider benefits include reduced expenses associated with the manual printing, scanning and faxing of documents, including paper and ink costs, as well as the maintenance of associated office machinery; the physical mailing of patient charts and records, and phone communication to verify delivery of traditional communications, referrals, and test results; and, the time and effort involved in recovering missing patient information, including any duplicate tests required to recover such information.

Exchanges in the United States must operate with patient consent to comply with not only the Health Insurance Portability and Accountability Act (HIPAA), but a variety of state and federal laws and regulations. This was clarified by the Office of Civil Rights in the January 2013 Final Omnibus Rule Update to HIPAA. There are two methods for gaining patient consent. One is explicit consent and is termed opt-in. With this method a patient is not automatically enrolled into the HIE by default and generally must submit a written request to join the exchange. The other method is implicit patient consent and is termed opt-out. In this method patients give implicit consent to join an HIE when they agree to use the services of a health care provider who is submitting data into an HIE and sign the provider's Notice of Privacy Practices. In this model patients can request to opt out of the HIE, generally with a written form.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions executed by the at least one processor to cause the at least one processor to implement the method, which comprises receiving a request, from a requestor device via a close proximity communication protocol, requesting to access an electronic medical record (EMR) associated with a patient. The method further comprises receiving user input via a user interface specifying conditions for permitting access to the EMR associated with the patient. The method further comprises transmitting an access authorization request to a patient registry system requesting the patient registry system to provide access to the EMR associated with the patient in accordance with the conditions for permitting access specified by the user input. The patient registry system generates a temporary access data structure based on the specified conditions. The patient registry system processes a subsequent request from the requestor device to access the EMR associated with the patient in accordance with the temporary access data structure.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 3 is a block diagram of a mechanism for implementing localized device specific limitations on access to patient medical information in accordance with an illustrative embodiment;

FIG. 4 is a flowchart illustrating operation of an authorizing user device for gathering and accessing medical information in accordance with an illustrative embodiment;

FIG. 5 is a flowchart illustrating operation of an authorizing user device for temporarily authorizing access to an electronic medical record in accordance with an illustrative embodiment;

FIG. 6 is a flowchart illustrating operation of a requesting device for requesting temporary access to a patient's electronic medical record in accordance with an illustrative embodiment; and FIG. 7 is a flowchart illustrating operation of a patient registry system implementing localized device specific limitations on access to patient medical information in accordance with an illustrative embodiment.

DETAILED DESCRIPTION

Figure 1:
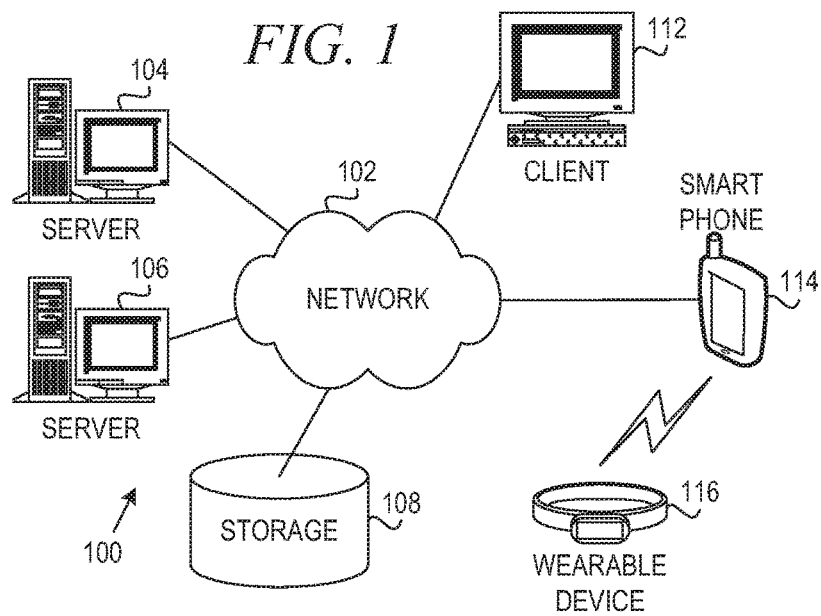
FIG. 1 is an example diagram of a distributed data processing system in which aspects of the illustrative embodiments may be implemented.

Protecting the privacy of a person's medical information, as may be stored in an electronic medical record (EMR), is of significant importance in any medical system to not only protect the patient but also to avoid liability under federal law. Various mechanisms have been developed for controlling access to medical information and ensuring privacy of a patient's medical data by implementing access control lists, data anonymization, and the like. The illustrative embodiments described herein are directed to providing personalized control over access to a patient's medical data such that the patient, or a person authorized by the patient, is able to control what particular individuals are permitted access to the patient's medical information, how long the access is allowed to occur, and on what specific device or devices the access may occur.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
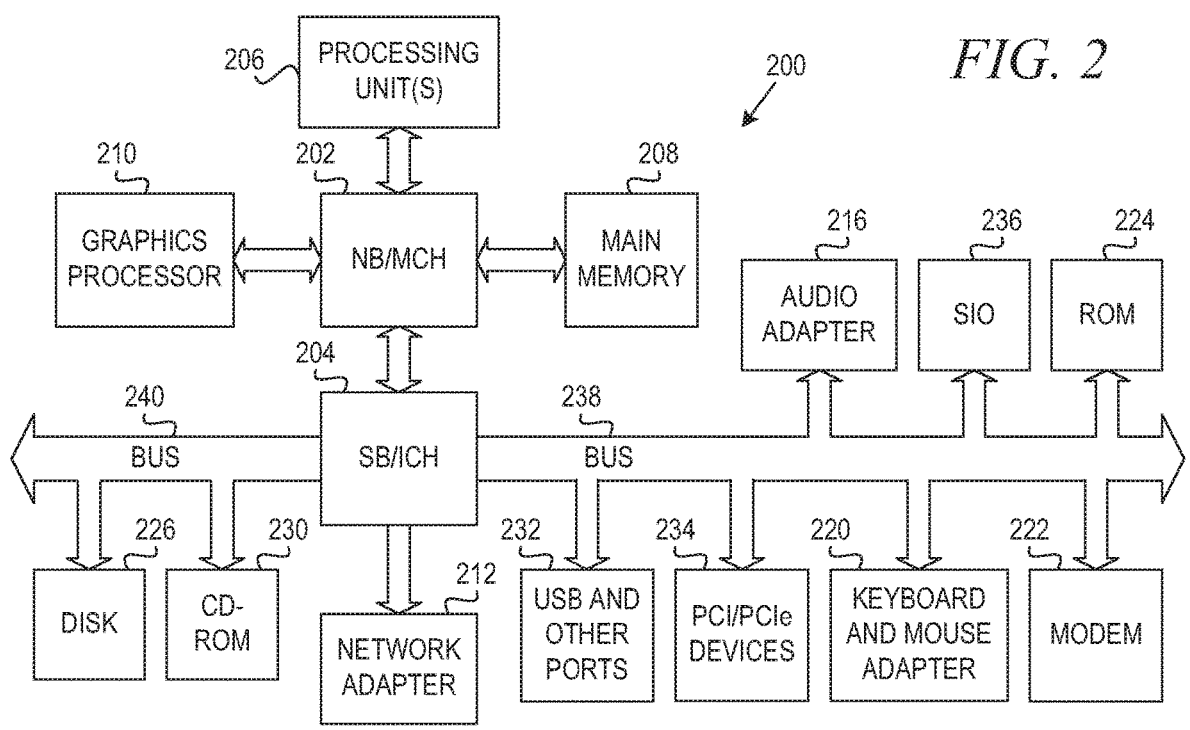
FIG. 2 is an example block diagram of a computing device in which aspects of the illustrative embodiments may be implemented.

The illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, client 112 and smart phone 114 are also connected to network 102. Client 112 and smart phone 114 may be, for example, personal computers, network computers, or the like. In the depicted example, servers 104 and 106 provide data, such as boot files, operating system images, and applications to the client 112 and smart phone 114. Client 112 and smart phone 114 are clients to servers 104, 106 in the depicted example. Distributed data processing system 100 may include additional servers, clients, and other devices not shown.

Wearable device 116 communicates with smart phone 114 using a communications link, such as Universal Serial Bus (USB), Bluetooth® communication, or the like. Common wearable devices include fitness tracking devices, step counters, smart watches, and specific health monitoring devices. Wearable devices and similar devices make up what is referred to as the "Internet of Things." These similar devices may include Wi-Fi connected scales, for example. These wearable devices and similar devices communicate with a user device, such as a smart phone, personal computer, or tablet, using wired or wireless (e.g., Wi-Fi or Bluetooth®) communication to upload information to the user device. The information may include, for example, steps taken, stairs climbed, heart rate history information, weight, body composition, blood pressure, etc. In the depicted example, wearable device 116 communicates monitored information to smart phone 114 via a wireless communication technology. Furthermore, a user may enter other medical information, such as foods eaten and the like, into smart phone 114.

In accordance with an embodiment, smart phone 114 uploads collected medical information to a patient registry system or health information exchange (HIE) on a server, such as server 104 or 106. In one embodiment, smart phone 114 or a personal computer, such as client 112, uploads medical information to a cloud service. In the depicted example, server 104 or 106 may then store the medical information in an EMR in storage 108.

In accordance with an illustrative embodiment, the user may access the EMR in storage 108. In addition, medical professionals with proper authorization access the EMR using a computer, such as client 112.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 104, may be specifically configured to implement localized device specific limitations on access to patient medical information. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates localized device specific limitations on access to patient medical information.

The mechanisms of the illustrative embodiments predicate access, by a particular person or device, upon a close proximity range (e.g., Bluetooth®, Near Field Communication (NFC), Infrared (IR) signals, or the like) exchange of information between a device that will be used to access a portion of the patient's EMR and a device associated with the patient himself/herself, or a device associated with an authorized individual that has been previously authorized to act on behalf of the patient. The authorizing device instructs the patient registry, such as a Health Information Exchange (HIE) system, who can access what portion of the patient's EMR, what device can be used to perform the access, and how long the access is allowed to occur. In this way, only specific devices associated with specific individuals are allowed to access portions of the patient's EMR specifically at the instruction of the patient or authorized individual and only for a specified duration.

As noted above, the mechanisms of the illustrative embodiments utilize specifically configured computing devices, or data processing systems, to perform the operations for implementing localized device specific limitations on access to patient medical information. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external affects of the illustrative embodiments as described herein.

In the depicted example, data processing system 200 employs a hub architecture including north bridge and memory controller hub (NB/MCH) 202 and south bridge and input/output (V/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System p® computer system, Power™ processor based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described hereafter with regard to the mechanisms for implementing localized device specific limitations on access to patient medical information.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is a block diagram of a mechanism for implementing localized device specific limitations on access to patient medical information in accordance with an illustrative embodiment. Health Information Exchange (HIE) system 320 stores and provides access to storage 330, in which a patient electronic medical record (EMR) 331 is stored. HIE system 320 includes authentication component 321 and access control component 322, which execute on one or more processors of HIE system 320.

In the depicted example, wearable device 315 and authorizing user device 310 communicate using a close proximity communication protocol, such as Bluetooth®, Wearable device 315 sends medical information to authorizing device 310. Wearable device 315 may be a fitness band, smart watch, step counter inserted in a shoe, or the like; however, alternatively device 315 may be a device such as a Wi-Fi connected smart scale. Thus, authorizing user device 310 may collect steps taken, stairs climbed, heartrate information, weight, body composition information, or the like. Authorizing user device 310 may then send the medical data to HIE system 320 to be stored in the patient's EMR 331. In the depicted example, authorizing user device 310 may be a smart phone, tablet computer, personal computer, laptop computer, or the like.

In accordance with an illustrative embodiment, the authorizing user device 310 accesses the patient's EMR 331 through HIE system 320. Authentication component 321 authenticates the source of the EMR access request. Access control component 322 controls access to EMR 331 based on user identification, device identification, device type, or the like using access control list (ACL) and/or temporary access permission list (TAPL) 332.

In the depicted example, a user or automated system that wishes to access a portion of a patient's EMR 331 must request access from a local device associated with the patient or authorized individual through a close proximity communication protocol, such as Bluetooth®, Infrared (IR) signaling, or other known close proximity communication protocol. In step 1, the requesting device 340 and the authorizing device 310 exchange information, such as via a handshake operation, such that the authorizing device 310 gathers device identifier information, device type information, user information for all authorized or registered users of the requesting device 340, and the like.

In step 2, this information may then be used by an application executing on the authorizing device 310 to create a user interface 311 through which the user of the authorizing device 310 can construct a request to the patient registry to allow the requesting device 340 to have access to a portion of the patient's EMR 331. The user interface 311 may provide user interface elements for allowing the user to specify which portions of the patient's EMR 331 are to be accessed (e.g., lab reports, patient history information, patient demographic information, entire EMR, etc.), which device and/or device type is allowed to perform the access, which users of the selected device are permitted to access the portion of the patient EMR, and the duration for which the access is to be allowed. In one embodiment, user interface 311 may receive user input, which may be a voice command, a finger print that has predefined conditions specified, or a dialog to get the conditions. In step 3, this information may be used by request generation component 312, which executes on at least one processor of authorizing user device 310, to construct an EMR access authorization request that is sent to the patient registry, or HIE system 320, to permit access to the specified portion of the patient's EMR to the requesting device for the specifically identified users for the specified period of time.

In step 4, at the patient registry or HIE system 320, authentication component 321 authenticates the source of the EMR access authorization request. That is, authentication component 321 authenticates the source device and the source user of the source device, against information associated with the patient EMR 331 to which access is requested. For example, the patient and/or one or more other authorized individuals (e.g., doctors, spouses, persons with medical power of attorney, etc.) may have their own authorization information (name, passcode/password, biometric information, etc.) associated with the patient's EMR 331, which can be used to authenticate the user of authorizing device 310. The authorizing device 310 may have a unique identifier, e.g., a media access control (MAC) address, serial number, etc., which uniquely identifies the device and which may also be registered with the patient EMR 331. In this way, the HIE system 320 determines whether the authorization request originated from an authorized device for accessing, or authorizing access to, the specific patient EMR 331.

Having authorized the source of the EMR access request, the patient registry registers a temporary access permission for the device identifier, device type, user identity, portion of the EMR, and time period specified in the EMR access authorization request in step 5. HIE system 320 stores the temporary access permission in ACL/TAPL 332 in storage 330. HIE system 320 uses this information when a device attempts to access the patient EMR 331 to determine whether such access is granted or denied.

Requesting device 340 includes user interface 341, which allows a user of requesting device 340 to generate a request for access to patient EMR 331. In step 6, requesting device 340 sends an access request to HIE system 320. In one embodiment, the request for access to the patient EMR contains the category for medical data from the EMR to be requested. For example, a pharmacist may only need Demographics, Allergies, and Medications, while a nurse may need Vitals only (e.g., Blood Pressure, Height Weight). This requested category of metadata may drive the acceptance and the data to be sent by the patient to the EMR company or any dialog or confirmation to make this easier and usable.

In step 7, HIE system 320 first attempts to authenticate the request using the primary access control list 332, which specifies the permanent access authorizations associated with the patient EMR 331, e.g., the patient, those with medical power of attorney, etc. Assuming the access request does not originate from one of those individuals who have permanent access permissions in the ACL, access control component 322 checks the temporary access permissions list to determine whether the device identifier, device type, and user identifier match an entry in the temporary access permissions list. In response to determining there is a match, access control component 322 checks the current time against the time period specified in the entry to determine whether the access time period has expired. If the access time period has not expired, then HIE system 320 returns a response to requesting device 340 providing access to the specified portion of the patient EMR 331 specified in the entry in the temporary access permissions list. If the time period has expired, then HIE system 320 returns a response informing the requesting device 340 that the access time period has expired. If any of the device identifier, device type, or user identifier does not match, then HIE system 320 returns a response indicating that access is denied.

An example scenario of the operation of the illustrative embodiments involves a patient in a new doctor's office, such as a specialist or someone the patient has not previously met with, where the patient can use a smart phone to authorize the doctor's access to the patient's EMR at the patient registry or HIE system for use during the appointment. The illustrative embodiments require physical proximity of the patient's smart phone or other mobile device to the doctor's computing system to permit the access to occur and can limit the access to the duration of the visit as well as limit access to specific devices and a specified user, e.g., the doctor.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

FIG. 4 is a flowchart illustrating operation of an authorizing user device for gathering and accessing medical information in accordance with an illustrative embodiment. Operation begins (block 400), and the authorizing user device gathers medical information from a wearable device, a Wi-Fi connected device, a device for monitoring specific health information, or from the user (e.g., gathering foods eaten) (block 401). The authorizing user device then authenticates with the Health Information Exchange (HIE) system (block 402) and stores the medical information at the HIE system or patient registry (block 403). Optionally, the authorizing user device may also access the medical information from the HIE system (block 404). Thereafter, operation ends (block 405).

FIG. 5 is a flowchart illustrating operation of an authorizing user device for temporarily authorizing access to an electronic medical record in accordance with an illustrative embodiment. Operation begins (block 500), and the authorizing device performs a handshake operation with the requesting device via a close proximity communication protocol (block 501). The authorizing device receives device information, e.g., device identifier, device type, and one or more user identifiers, from the requesting device (block 502). The authorizing device provides user interface elements to allow the user to specify one or more portions of the EMR to be accessed, which device or device type, and for how long access to the medical information is to be allowed (block 503).

Then, the authorizing device generates an authorization request (block 504) and sends the authorization request to the HIE system (block 505). Assuming the HIE system successfully authenticates the authorizing device, the authorizing user device receives acknowledgement (block 506). The authorizing user device then sends access information to the requesting device indicating an address and/or identification of the EMR (block 507). Thereafter, operation ends (block 508).

FIG. 6 is a flowchart illustrating operation of a requesting device for requesting temporary access to a patient's electronic medical record in accordance with an illustrative embodiment. Operation begins (block 600), and the requesting device performs a handshake operation with the authorizing device via a close proximity communication protocol (block 601). The requesting device sends device information, e.g., device identifier, device type, and one or more user identifiers, to the authorizing user device (block 602). The requesting device then receives medical record access information from the authorizing user indicating an address and/or identification of the EMR (block 603). The requesting device sends a medical record access request to the HIE system (block 604) and receives a response from the HIE system (block 605).

The requesting device determines whether the access request was denied (block 606). The HIE system may deny the access request because of an authentication failure, because no match was found in the temporary access permissions list, or because the access time period has expired. If the access request was not denied, then the requesting device presents the medical record in a user interface to the requestor (block 607). Thereafter, or if the access request was denied in block 606, operation ends (block 608).

FIG. 7 is a flowchart illustrating operation of a patient registry system implementing localized device specific limitations on access to patient medical information in accordance with an illustrative embodiment. Operation begins (block 700), and the patient registry system or HIE system receives an authorization request from an authorized user device (block 701). The authorization request specifies a portion of the EMR to be accessed and specifies at least one device ID, a device type, and at least one user ID for which access to the specified portion of the EMR is to be granted. The authorization request also specifies a time period for which the access is to be allowed. The HIE system authenticates the authorization request against information associated with the electronic medical record for which temporary authorization is being requested (block 702). Assuming authentication is successful, the HIE system generates a temporary access permission (block 703) and stores the temporary access permission as an entry in a temporary access permissions list (block 704).

Then, the HIE system receives an access request from a requesting device (block 705). The HIE system checks the device ID, device type, and user ID against the temporary access permissions list (block 706) and determines whether they match an entry in the temporary access permissions list (block 707). In response to the HIE system determining there is a match, the HIE system checks the current time against the time period specified in the entry (block 708) and determines whether the specified time period has expired (block 709). In response to the time period not having expired, the HIE system returns a response to the requesting device providing access to the specified portion of the EMR (block 710). Thereafter, operation ends (block 711).

In response to the HIE determining that at least one of the device ID, the device type, or the user ID does not match an entry in the temporary access permissions list in block 707 or determining that the specified time period has expired in block 709, the HIE system returns a response to the requesting device denying access to the specified portion of the EMR (block 712). Thereafter, operation ends (block 711).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement the method which comprises:

receiving, at an authorizing user device, collected medical information from a wearable device associated with a patient;

authenticating the authorizing user device with a patient registry system and storing the collected medical information in an electronic medical record (EMR) associated with the patient in the patient registry system;

receiving, at the authorizing user device from a requestor device via a close proximity communication protocol, a request to access the collected medical information in the EMR, wherein the request comprises a device identifier of the requester device;

receiving, from the authorizing user at the authorizing user device, user input specifying conditions for permitting access to the collected medical information by the requestor device;

transmitting an access authorization request from the authorizing user device to a patient registry system requesting the patient registry system to provide access to the collected medical information in accordance with the conditions for permitting access specified by the user input, wherein the access authorization request specifies the device identifier of the requestor device and a time period during which access is to be permitted to the requestor device;

authenticating the access authorization request with the patient registry system based on a unique identifier of the authorizing user device and biometric information of the authorizing user;

responsive to the patient registry system storing a temporary access data structure for permitting temporary access to the collected medical information for the requester device in accordance with the access authorization request, receiving an acknowledgement at the authorizing user device from the patient registry system; and transmitting access information for accessing the collected medical information from the authorizing user device to the requestor device, wherein the access information comprises an address of the EMR associated with the patient.

2. The method of claim 1, wherein the user input is received via a user interface comprising a user interface element for specifying a portion of the patient EMR to which access is permitted, wherein the specified portion comprises the collected medical information.

3. The method of claim 2, wherein the user interface comprises a user interface element for specifying which devices are authorized to access the specified portion of the patient EMR.

4. The method of claim 1, wherein the request for access to the patient EMR contains a category for medical data from the EMR to be requested.

5. The method of claim 1, wherein the user input is a preconfigured set of conditions verified by biometric indication or voice command by the user.

6. The method of claim 1, wherein the conditions for permitting access comprise an identifier of one or more portions of the EMR that may be accessed and a user identity of a user that is permitted to access the one or more portions of the EMR.

7. A computer program product comprising a computer readable storage medium having a computer readable program stored therein, wherein the computer readable program, when executed on a computing device, causes the computing device to:

receive, at an authorizing user device, collected medical information from a wearable device associated with a patient;

authenticate the authorizing user device with a patient registry system and store the collected medical information in an electronic medical record (EMR) associated with the patient in the patient registry system;

receive, at the authorizing user device from a requestor device via a close proximity communication protocol, a request to access the collected medical information in the EMR, wherein the request comprises a device identifier of the requestor device;

receive, from the authorizing user at the authorizing user device, user input specifying conditions for permitting access to the collected medical information by the requestor device;

transmit an access authorization request from the authorizing user device to a patient registry system requesting the patient registry system to provide access to the collected medical information in accordance with the conditions for permitting access specified by the user input, wherein the access authorization request specifies the device identifier of the requestor device and a time period during which access is to be permitted to the requestor device;

authenticate the access authorization request with the patient registry system based on a unique identifier of the authorizing user device and biometric information of the authorizing user;

responsive to the patient registry system storing a temporary access data structure for permitting temporary access to the collected medical information for the requestor device in accordance with the access authorization request, receive an acknowledgement at the authorizing user device from the patient registry system; and transmit access information for accessing the collected medical information from the authorizing user device to the requestor device, wherein the access information comprises an address of the EMR associated with the patient.

8. The computer program product of claim 7, wherein the user input is received via a user interface comprising a user interface element for specifying a portion of the patient EMR to which access is permitted, wherein the specified portion comprises the collected medical information.

9. The computer program product of claim 8, wherein the user interface comprises a user interface element for specifying which devices are authorized to access the specified portion of the patient EMR.

10. The computer program product of claim 7, wherein the user input is a preconfigured set of conditions verified by biometric indication or voice command by the user.

11. The computer program product of claim 7, wherein the conditions for permitting access comprise an identifier of one or more portions of the EMR that may be accessed and a user identity of a user that is permitted to access the one or more portions of the EMR.

12. An apparatus comprising:
a processor; and
a memory coupled to the processor, wherein the memory comprises instructions which, when executed by the processor, cause the processor to:
receive, at an authorizing user device, collected medical information from a wearable device associated with a patient;
authenticate the authorizing user device with a patient registry system and store the collected medical information in an electronic medical record (EMR) associated with the patient in the patient registry system;
receive, at the authorizing user device from a requestor device via a close proximity communication protocol, a request to access the collected medical information in the EMR, wherein the request comprises a device identifier of the requestor device;
receive, from the authorizing user at the authorizing user device, user input specifying conditions for permitting access to the collected medical information by the requestor device;
transmit an access authorization request from the authorizing user device to a patient registry system requesting the patient registry system to provide access to the collected medical information in accordance with the conditions for permitting access specified by the user input, wherein the access authorization request specifies the device identifier of the requestor device and a time period during which access is to be permitted to the requestor device;
authenticate the access authorization request with the patient registry system based on a unique identifier of the authorizing user device and biometric information of the authorizing user;
responsive to the patient registry system storing a temporary access data structure for permitting temporary access to the collected medical information for the requestor device in accordance with the access authorization request, receive an acknowledgement at the authorizing user device from the patient registry system; and
transmit access information for accessing the collected medical information from the authorizing user device to the requestor device, wherein the access information comprises an address of the EMR associated with the patient.

13. The method of claim 1, further comprising:
receiving, by the patient registry system, the access authorization request;
authenticating, by the patient registry system, the access authorization request against information associated with the EMR; and
generating the temporary access data stricture for permitting access to the collected medical information for the requestor device in accordance with the access authorization request.

14. The method of claim 13, further comprising:
sending, by the requestor device, a medical record access request to the patient registry system;
authenticating, by the patient registry system, the medical record access request against the temporary access data structure; and
responsive to the medical access request matching information in the temporary access data structure, returning a response providing access to the collected medical information associated with the patient from the patient registry system to the requestor device.

15. The method of claim 14, wherein authenticating the medical record access request comprises determining whether a time period specified in the temporary access data structure has expired.

16. The method of claim 15, further comprising:
responsive to the medical access request not matching information in the temporary access data structure or the time period being expired, returning a response denying access to the collected medical information associated with the patient from the patient registry system to the requestor device.

17. The method of claim 14, further comprising:
responsive to the requestor device receiving the response providing access to the collected medical information, presenting at least a portion of the collected medical information in a user interface of the requestor device.

18. The method of claim 1, wherein the wearable device comprises a fitness band, a smart watch, a step counter inserted in a shoe, or a smart scale.

19. The method of claim 18, wherein the collected medical information comprises steps taken, stairs climbed, heart-rate information, weight, or body composition information.

* * * * *